(12) United States Patent
Itescu et al.

(10) Patent No.: US 11,312,941 B2
(45) Date of Patent: *Apr. 26, 2022

(54) STEM CELL COMPOSITION

(71) Applicant: Mesoblast International Sarl, Meyrin (CH)

(72) Inventors: Silviu Itescu, Melbourne (AU); Paul Simmons, Melbourne (AU)

(73) Assignee: MESOBLAST INTERNATIONAL SARL, Meyrin (CH)

( * ) Notice: Subject to any disclaimer, the term of this patent is extended or adjusted under 35 U.S.C. 154(b) by 80 days.

This patent is subject to a terminal disclaimer.

(21) Appl. No.: 16/434,726

(22) Filed: Jun. 7, 2019

(65) Prior Publication Data

US 2019/0345452 A1 Nov. 14, 2019

Related U.S. Application Data

(63) Continuation of application No. 15/300,716, filed as application No. PCT/EP2015/057521 on Apr. 7, 2015, now Pat. No. 10,400,218.

(30) Foreign Application Priority Data

Apr. 7, 2014 (AU) ................................ 2014901247

(51) Int. Cl.
*C12N 5/0775* (2010.01)
*A61K 35/28* (2015.01)

(52) U.S. Cl.
CPC ............ *C12N 5/0663* (2013.01); *A61K 35/28* (2013.01); *C12N 2500/38* (2013.01); *C12N 2501/39* (2013.01)

(58) Field of Classification Search
CPC ... C12N 5/0663; C12N 2500/38; A61K 35/28
See application file for complete search history.

(56) References Cited

U.S. PATENT DOCUMENTS

2017/0107495 A1 4/2017 Itescu et al.

FOREIGN PATENT DOCUMENTS

| CN | 102899293 A | 1/2013 |
|---|---|---|
| JP | 2006-521121 A | 9/2006 |
| JP | 2008-514188 A | 5/2008 |
| JP | 2012-528643 | 11/2012 |
| WO | WO 2004/074494 A1 | 9/2004 |

OTHER PUBLICATIONS

International Search Report in connection with PCT International Application No. PCT/EP2015/057521.
Written Opinion of the International Searching Authority in connection with PCT International Application No. PCT/EP2015/057521.
Antonio Sorrentino, et al., "Isolation and characterization of CD146<+> multipotent mesenchymal stromal cells", Experimental Hematology, Aug. 1, 2008, vol. 36, No. 8, Elsevier Inc., US.
Xiaohui Fang, et al., "Allogenic Human Mesenchymal Stem Cells Restore Epithelial Protein Permeability in Cultured Human Alveolar Type II Cells by Secretion of Angiopoietin-1", Journal of Biological Chemistry, Aug. 20, 2010, vol. 285, No. 34, US.
Paola Romina Amable, et al., "Gene expression and protein secretion during human mesenchymal cell differentiation into adipogenic cells", BMC Cell Biology, Dec. 20, 2014, vol. 15, No. 1, BioMed Central, London, GB.
D.S. Bischoff, et al., "Angiogenic CXC Chemokine Expression During Differentiation of Human Mesenchymal Stem Cells Towards the Osteoblastic Lineage", Journal of Cellular Biochemistry, Jan. 1, 2008, vol. 103, No. 3, Wiley-Liss, Inc.
Shirley H. J. Mei, et al., "Prevention of LPS-Induced Acute Lung Injury in Mice by Mesenchymal Stem Cells Overexpressing Angiopoietin 1", Circulation Research, Jan. 1, 2007, vol. 98, No. 9, PLoS Medicine.
Adam Oskowitz, et al., "Serum-deprived human multipotent mesenchymal stromal cells (MSCs) are highly angiogenic", Stem Cell Research, Jan. 31, 2011, vol. 6, No. 3, Elsevier, NL.
Christian Sundberg, et al., "Stable Expression of Angiopoietin-1 and Other Markers by Cultured Pericytes: Phenotypic Similarities to a Subpopulation of Cells in Maturing Vessels During Later Stages of Angiogenesis In Vivo", Laboratory Investigation, Apr. 1, 2002, vol. 82, No. 4.
J. Xu, et al., "Mesenchymal stem cell-based angiopoietin-1 gene therapy for acute lung injury induced by lipopolysaccharide in mice", The Journal of Pathology, Mar. 11, 2008, vol. 214, No. 4.
Jei Keon Chae, et al., "Coadministration of Angiopoietin-1 and Vascular Endothelial Growth Factor Enhances Collateral Vascularization", Arteriosclerosis, Thrombosis, and Vascular Biololgy, Dec. 1, 2000, vol. 20, No. 12, Lippincott Williams & Wilkins, US.
Le Cao, et al., "Experimental repair of segmental bone defects in rabbits by angiopoietin-1 gene transfected MSCs seeded on porous β-TCP scaffolds", Journal of Biomedical Materials Research, Jul. 2012, vol. 100B, No. 5.
Sun Lijie, et al., "Mesenchymal stem cells modified with angiopoietin-1 improve remodeling in a rat model of acute myocardial infarction", Biochemical and Biophysical Research Communications, Apr. 27, 2007, vol. 357, No. 3, Academic Press Inc., Orlando, FL, US.

(Continued)

*Primary Examiner* — Taeyoon Kim
(74) *Attorney, Agent, or Firm* — John P. White (57) ABSTRACT

The disclosure provides stem cells which express high levels of Angeopoetin-1 (Ang1) and methods for their production. Such stem cells may be used in a range of therapeutic applications.

7 Claims, 3 Drawing Sheets

(56) References Cited

OTHER PUBLICATIONS

Hyongbum Kim, et al., "Dexamethasone increases angiopoietin-1 and quiescent hematopoietic stem cells: A novel mechanism of dexamethasone-induced hematoprotection", FEBS Letters, Oct. 15, 2008, vol. 582, No. 23-24, Elsevier, Amsterdam, NL.
"Surface Areas and Recommended Medium Volumes for Corning Cell Culture Vessels", Corning Life Sciences, Sep. 15, 2008, Corning, NY, US.
IMIC (2011) vol. 32-3, pp. 49-53.
Kazama, T., "Basic Research and Clinical Application in Mesenchymal Stem Cells". J. Nihon Univ. Med. Ass., 2016, vol. 75(2), pp. 61-66.

STEM CELL COMPOSITION

This application is a continuation of U.S. application Ser. No. 15/300,716, filed Sep. 29, 2016, now allowed, a § 371 national stage of PCT International Application No. PCT/EP2015/057521, filed Apr. 7, 2015, claiming priority of Australian Patent Application No. AU 2014901247, filed Apr. 7, 2014, the content of each of which are hereby incorporated by reference into the application.

TECHNICAL FIELD

The present disclosure relates to stem cells which express high levels of Angeopoetin-1 (Ang1) and methods for their production. Such stem cells may be used in a range of therapeutic applications, for example, to promote vascularisation and/or angiogenesis.

BACKGROUND

Angiopoietin is part of a family of vascular growth factors that play a role in embryonic and postnatal angiogenesis. Ang1 promotes migration of endothelial and some non-endothelial cells such as smooth muscle cells. Ang1 also induces sprouting and reorganisation of endothelial cells into tubules. Ang1 exerts potent anti-inflammatory effects on endothelial cells, suppressing Vascular Endothelial Growth Factor (VEGF) induced upregulation of E-selectin, ICAM-1 and VCAM-1, and inhibiting leucocyte adhesion and transmigration in response to VEGF and TNF-α (Kim et al. 2001a).

Many studies have shown that overexpression of Ang1, or the addition of supplemental Ang1, leads to beneficial effects in relieving ischemia and restoring the function of several organs, including limbs, brain, articular joints, kidneys and most significantly, in the heart. Other beneficial effects include reliving thrombosis (Kim et al. 2001b). Accordingly, Ang1 exhibits a number of key properties that would suggest its utility as a therapeutic for cardiovascular disease.

Amongst the cascade of growth factors required for the development of a functional vascular system, Ang1 and VEGF fulfil central roles. Accordingly, for therapeutic vascularization in the treatment of ischemic myocardium the use of Ang1 in combination with VEGF is also viewed as a highly promising candidate.

Previously, the combined administration of Ang1 and VEGF-A into myocardial infract or peri-infarct zones in test animals has been shown to increase neovascularization and reduce myocardial apoptosis, leading to increased cardiomyocyte regeneration at the injection sites, as well as improved vascular perfusion and cardiac function. Submaximal doses of Ang1 and VEGF at a ratio of about 20:1 enhanced these effects and was more potent than that of either factor alone (Chae et al. 2000). These results show that combined treatment of Ang1 and VEGF could be used to produce therapeutic vascularization.

Recently, stem cell therapy has emerged as one of the potential treatments for ischemic heart disease (Huang et al. 2011; Lijie et al. 2007).

The use of stem cells alone to promote angiogeneisis remains limited because of insufficient expression of angiogenic factors in many types of stem cells. Genetic modification of stem cells, involving transfection of stem cells with a nucleic acid molecule encoding Ang1, has been employed to address this limitation. The use of genetically modified stem cells has its drawbacks, however, due to complexities with the technology and potentially undesirable effects caused by the genetic modification process.

SUMMARY OF THE INVENTION

The present disclosure is based on the unexpected production of a population of stem cells that express Ang1 at high levels without the need for transfection of the cells with a nucleic acid expressing Ang1. In one example, this population of the stem cells also expresses VEGF at low levels and the ratio of Ang1:VEGF produced was consistent with the ratio shown by Chae et al. (2000) to be particularly effective in enhancing vascularization.

Accordingly, the present disclosure provides a composition comprising genetically unmodified stem cells, wherein said genetically unmodified stem cells express Ang1 in an amount of at least 0.1 µg/$10^6$ cells.

In another example, the composition comprises stem cells expressing Ang1 in an amount of at least 0.5 µg/$10^6$ cells. In another example, the stem cells express Ang1 in an amount of at least 0.7 µg/$10^6$ cells. In another example, the stem cells express Ang1 in an amount of at least 1 µg/$10^6$ cells.

In another example, the stem cells express VEGF in an amount less than about 0.05 µg/$10^6$ cells. In another example, the stem cells express VEGF in an amount less than about 0.03 µg/$10^6$ cells. In another example, the stem cells express VEGF in an amount less than about 0.02 µg/$10^6$ cells.

In another example, the genetically unmodified stem cells express Ang1:VEGF at a ratio of at least about 2:1. In another example, the genetically unmodified stem cells express Ang1:VEGF at a ratio of at least about 10:1. In another example, the stem cells express Ang1:VEGF at a ratio of at least about 20:1. In another example, the stem cells express Ang1:VEGF at a ratio of at least about 30:1. In another example, the stem cells express Ang1:VEGF at a ratio of at least about 50:1.

In another example, the stem cells are mesenchymal stem cells. In another example, the stem cells are mesenchymal precursor cells. In another example, the stem cells are derived from induced pluripotent stem cells (iPS cells).

In another example, the composition further comprising an acceptable pharmaceutical carrier.

In another example the composition is produced by culturing genetically unmodified stem cells according to the method described below.

The present disclosure also provides an in vitro method for inducing Ang1 expression in stem cells, the method comprising: culturing a population of stem cells in a cell culture media, wherein the cell culture media:
  contains a short acting L-ascorbic acid derivative but does not contain a substantial amount of a long acting L-ascorbic acid derivative; and/or
  is supplemented with less than 10% v/v fetal calf serum.

The present disclosure also provides an in vitro method for inducing Ang1 expression in stem cells, the method comprising: culturing a population of stem cells in a cell culture media, wherein the cell culture media:
  contains a short acting L-ascorbic acid derivative but does not contain a substantial amount of a long acting L-ascorbic acid derivative; and/or
  is supplemented with less than 10% v/v fetal calf serum; and/or
  is supplemented with anon-fetal serum.

In one example, the above method further comprises measuring the Ang1 levels to determine that Ang1 expression is induced. In another example, Ang1 expression is induced when the stem cells express Ang1 in an amount of at least 0.5 µg/$10^6$ cells. In another example, Ang1 expression is induced when the stem cells express Ang1 in an amount of at least 0.7 µg/$10^6$ cells. In another example, Ang1 expression is induced when the stem cells express Ang1 in an amount of at least 1 µg/$10^6$ cells.

In one example, the above method further comprises selecting cells with induced Ang1 expression. In one example, cells which express Ang1 in an amount of at least 0.5 µg/$10^6$ cells are selected. In another example, cells which express Ang1 in an amount of at least 0.7 µg/$10^6$ cells are selected. In another example, cells which express Ang1 in an amount of at least 1 µg/$10^6$ cells are selected.

In one example, the method further comprises measuring the Ang1 levels to determine that Ang1 expression is induced and selecting cells with induced Ang1 expression.

In one example, the short acting ascorbic acid derivative is a L-ascorbic acid salt.

In one example, the short acting ascorbic acid derivative is a L-ascorbic acid sodium salt.

In one example, the cell culture media is supplemented with less than 10% v/v fetal calf serum (FCS).

In one example, the cell culture media is supplemented with less than 8% v/v fetal calf serum (FCS).

In one example, the cell culture media is supplemented with less than 7% v/v fetal calf serum (FCS).

In one example, the cell culture media is supplemented with less than 6% v/v fetal calf serum (FCS).

In one example, the cell culture media is supplemented with less than 5% v/v fetal calf serum.

In one example, the cell culture media is supplemented with one or more stimulatory factors selected from the group consisting of 1α,25-dihydroxyvitamin D3 (1,25D), platelet derived growth factor (PDGF), tumor necrosis factor α (TNF-α), interleukin-1β (IL-1β) and stromal derived factor 1α (SDF-1α).

In one example, the cell culture media is supplemented with a non-fetal serum.

In one example, the cell culture media is supplemented with mammalian non-fetal serum.

In one example, the cell culture media is supplemented with human non-fetal serum.

In one example, the cell culture media is supplemented with neo-natal serum.

In one, example, the cell culture medium is supplemented with mammalian neo-natal serum.

In one example, the cell culture media is supplemented with new born calf serum (NBCS).

In one example, the cell culture media is supplemented with human neo-natal serum.

In one example, the cell culture media is supplemented with human neo-natal serum obtained from umbilical cord blood.

In another example, the cell culture media is supplemented with adult serum.

In one example, the cell culture media is supplemented with mammalian adult serum.

In one example, the cell culture media is supplemented with adult bovine serum.

In one example, the cell culture media is supplemented with human adult serum.

In one example, the cell culture media is supplemented with human AB serum.

In another example, the cell culture media is supplemented with at least about 5% v/v NBCS.

In another example, the cell culture media is supplemented with at least about 2% v/v NBCS.

In one example, the cell culture media is supplemented with a mixture of NBCS and FCS. For example, the ratio of NBCS to FCS may be about 1:1.

In one example, the cell culture media is supplemented with at least about 5% v/v FCS and at least about 5% v/v NBCS.

In one example, the cell culture media is not supplemented with fetal serum.

The present disclosure also provides a method for obtaining genetically unmodified stem cells suitable for use in promoting vascularisation and/or angiogenesis, comprising: obtaining at least one cell population including stem cells from at least one donor; culturing the stem cells: determining the amount of Ang1 expressed by the stem cells in each of said at least one cell population(s); and selecting stem cells which express Ang1 in an amount of at least 0.1 µg/$10^6$ cells.

In one example the method further comprises determining the amount of VEGF expressed by the stem cells in each of said at least one cell population(s); and selecting stem cells which express Ang1:VEGF at a ratio of at least 2:1, or a ratio of at least 10:1, or a ratio of at least 20:1, or a ratio of at least 30:1, or a ratio of at least 50:1.

The present disclosure also provides use of a composition described herein for promoting vascularisation and/or angiogenesis. The present disclosure also provides use of a composition described herein as an anti-thrombotic. The present disclosure also provides use of a composition described herein for treating a condition in which increased Ang1 expression is desirable.

The present disclosure also provides a method for promoting vascularisation and/or angiogenesis in a subject, the method comprising administering to the subject a composition described herein. The present disclosure also provides a method for reducing thrombosis formation in a subject, the method comprising administering to the subject a composition described herein. The present disclosure also provides a method for treating a condition in which increased Ang1 expression is desirable in a subject, the method comprising administering to the subject a composition described herein.

The present disclosure also provides use of a composition described herein in the manufacture of a medicament for promoting vascularisation and/or angiogenesis. The present disclosure also provides use of a composition described herein in the manufacture of a medicament for reducing thrombosis formation. The present disclosure also provides for use of a composition described herein in the manufacture of a medicament for treating a condition in which increased Ang1 expression is desirable.

The stem cells described of the present disclosure can be obtained from any mammal. For example, the stem cells may be derived from a primate, a cow, sheep, horse, dog, cat, or goat. In one example, the stem cell are human stem cells.

In another example, the present disclosure relates to a population of stem cells cultured according to the methods of the present disclosure or obtained by the methods of the present disclosure.

In another example, the methods of the present disclosure are used in the manufacture of a medicament for promoting vascularisation and/or angiogenesis.

In another example, the methods of the present disclosure are used in the manufacture of a medicament for treating a condition in which increased Ang1 expression is desirable.

DETAILED DESCRIPTION

General Techniques and Definitions

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure, as described herein.

Any example disclosed herein shall be taken to apply mutatis mutandis to any other example unless specifically stated otherwise.

Unless specifically defined otherwise, all technical and scientific terms used herein shall be taken to have the same meaning as commonly understood by one of ordinary skill in the art (e.g., in cell culture, molecular genetics, stem cell differentiation, immunology, immunohistochemistry, protein chemistry, and biochemistry).

Unless otherwise indicated, the stem cells, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, of the designated value.

Volume percent (v/v %) defines [(volume of solute)/(volume of solution)]×100%. Volume percent is relative to the volume of solution. For example, cell culture media supplemented with 5% v/v FCS means there are about 5 ml FCS for every 100 ml of cell culture media.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Stem Cells

As used herein, the term "stem cell" refers to self-renewing cells that are capable of giving rise to phenotypically and genotypically identical daughters as well as at least one other final cell type (e.g., terminally differentiated cells). The term "stem cells" includes totipotential, pluripotential and multipotential cells, as well as progenitor and/or precursor cells derived from the differentiation thereof. The stem cell may be an adult or embryonic stem cell.

As used herein, the term "totipotent cell" or "totipotential cell" refers to a cell that is able to form a complete embryo (e.g., a blastocyst).

As used herein, the term "pluripotent cell" or "pluripotential cell" refers to a cell that has complete differentiation versatility, i.e., the capacity to grow into any of the mammalian body's approximately 260 cell types. A pluripotent cell can be self-renewing, and can remain dormant or quiescent within a tissue.

By "multipotential cell" or "multipotent cell" we mean a cell which is capable of giving rise to any of several mature cell types. As used herein, this phrase encompasses adult progenitor cells and multipotential progeny of these cells. Unlike a pluripotent cell, a multipotent cell does not have the capacity to form all of the cell types.

As used herein, the term "mesenchymal lineage precursor or stem cell" refers to cells that can differentiate into a mesenchymal cell type. For example, mesenchymal lineage precursor cells and mesenchymal precursor cells can differentiate into bone, cartilage, muscle and fat cells, and fibrous connective tissue.

In one example the stem cells of the present disclosure are STRO-1+ mesenchymal precursor cells.

STRO-1+ multipotential cells are cells found in bone marrow, blood, dental pulp, adipose tissue, skin, spleen, pancreas, brain, kidney, liver, heart, retina, brain, hair follicles, intestine, lung, lymph node, thymus, bone, ligament, tendon, skeletal muscle, dermis, and periosteum. Thus, STRO-1+ multipotential cells are capable of differentiating into a large number of cell types including, but not limited to, adipose, osseous, cartilaginous, elastic and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. In one embodiment STRO-1+ multipotential cells are non-hematopoietic progenitor cells which divide to yield daughter cells that are either stem cells or are precursor cells which in time will irreversibly differentiate to yield a phenotypic cell.

In one example, STRO-1+ cells are enriched from a sample obtained from a subject, e.g., a subject to be treated or a related subject or an unrelated subject (whether of the same species or different). The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for STRO-1+ cells comprises at least about 0.1% or 0.5% or 1% or 2% or 5% or 10% or 15% or 20% or 25% or 30% or 50% or 75% or 85% or 95% or 99% STRO-1+ cells. In this regard, the term "population of cells enriched for STRO-1+ cells" will be taken to provide explicit support for the term "population of cells comprising X % STRO-1+ cells", wherein X % is a percentage as recited herein. The STRO-1+ cells can, in some examples, form clonogenic colonies, e.g. CFU-F (fibroblasts) or a subset thereof (e.g., 50% or 60% or 70% or 80% or 90% or 95%) can have this activity.

In one example, the stem cells of the present disclosure are enriched from a cell preparation comprising STRO-1+ cells in a selectable form. In this regard, the term "selectable form" will be understood to mean that the cells express a marker (e.g., a cell surface marker) permitting selection of the STRO-1+ cells. The marker can be STRO-1, but need not be. For example, as described and/or exemplified herein, cells (e.g., MPCs) expressing STRO-2 and/or STRO-3 (TNAP) and/or STRO-4 and/or VCAM-1 and/or CD146 and/or 3G5 also express STRO-1 (and can be STRO-1$^{bright}$). Accordingly, an indication that cells are STRO-1+ does not mean that the cells are selected by STRO-1 expression. In one example, the cells are selected based on at least STRO-3 expression, e.g., they are STRO-3+(TNAP+). In another example, the cells are selected based on at least STRO-4 expression, e.g., they are STRO-4+.

Reference to selection of a cell or population thereof does not necessarily require selection from a specific tissue source. As described herein STRO-1+ cells can be selected from or isolated from or enriched from a large variety of sources. That said, in some examples, these terms provide support for selection from any tissue comprising STRO-1+ cells (e.g., MPCs) or vascularized tissue or tissue comprising pericytes (e.g., STRO-1+ pericytes) or any one or more of the tissues recited herein.

In one example, the stem cells of the present disclosure express one or more markers individually or collectively selected from the group consisting of STRO-1+, TNAP+, VCAM-1+, THY-1+, STRO-2+, STRO-4+(HSP-90β, CD45+, CD146+, 3G5+, CC9 or any combination thereof.

By "individually" is meant that the disclosure encompasses the recited markers or groups of markers separately, and that, notwithstanding that individual markers or groups of markers may not be separately listed herein the accompanying claims may define such marker or groups of markers separately and divisibly from each other.

By "collectively" is meant that the disclosure encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

In one example, STRO-1+ cells are STRO-1$^{bright}$ (syn. STRO-1$^{bri}$). In one example, the STRO-1$^{bri}$ cells are preferentially enriched relative to STRO-1$^{dim}$ or STRO-1$^{intermediate}$ cells.

In one example, STRO-1$^{bright}$ cells are additionally one or more of TNAP+, VCAM-1+, THY-1+, STRO-2+, STRO-4+(HSP-90β) and/or CD146+. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the STRO-1$^{bright}$ are isolated by immunoselection. In one example, STRO-1$^{bright}$ cells are isolated by immunoselection of cells expressing TNAP. As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

In one example, the mesenchymal precursor or stem cells are CD29+, CD54+, CD73+, CD90+, CD102+, CD105+, CD106+, CD166+, MHC1+ mesenchymal stem cells (e.g. remestemcel-L).

In one example, mesenchymal precursor cells are perivascular mesenchymal precursor cells as defined in WO 2004/85630. For example, the mesenchymal precursor cells express a marker of a perivascular cell, e.g., the cells are STRO-1+ or STRO-1$^{bright}$ and/or 3G5+. In one example, the cells are or were previously or are progeny of cells that were isolated from vascularized tissue or organs or parts thereof.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labelled or is undetectable above background levels, e.g., levels detected using an isotype control antibody.

The term "bright", when used herein, refers to a marker on a cell surface that generates a relatively high signal when detectably labelled. Whilst not wishing to be limited by theory, it is proposed that "bright" cells express more of the target marker protein (for example the antigen recognized by STRO-1) than other cells in the sample. For instance, STRO-1$^{bri}$ cells produce a greater fluorescent signal, when labelled with a FITC-conjugated STRO-1 antibody as determined by fluorescence activated cell sorting (FACS) analysis, than non-bright cells (STRO-1$^{dull/dim}$). In one example, "bright" cells constitute at least about 0.1% of the most brightly labelled bone marrow mononuclear cells contained in the starting sample. In other examples, "bright" cells constitute at least about 0.1%, at least about 0.5%, at least about 1%, at least about 1.5%, or at least about 2%, of the most brightly labelled bone marrow mononuclear cells contained in the starting sample. In an example, STRO-1$^{bright}$ cells have 2 log magnitude higher expression of STRO-1 surface expression relative to "background", namely cells that are STRO-1−. By comparison, STRO-1$^{dim}$ and/or STRO-1$^{intermediate}$ cells have less than 2 log magnitude higher expression of STRO-1 surface expression, typically about 1 log or less than "background".

In one example, a significant proportion of the STRO-1+ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another example, the STRO-1+ cells are not capable of giving rise, upon culturing, to hematopoietic cells.

In one example, the presently described stem cells are mesenchymal stem cells. The mesenchymal stem cells (MSC) may be a homogeneous composition or may be a mixed cell population enriched in MSCs. Homogeneous mesenchymal stem cell compositions may be obtained by culturing adherent marrow or periosteal cells, and the mesenchymal stem cells may be identified by specific cell surface markers which are identified with unique monoclonal antibodies. A method for obtaining a cell population enriched in mesenchymal stem cells is described, for example, in U.S. Pat. No. 5,486,359. Alternative sources for mesenchymal stem cells include, but are not limited to, blood, skin, cord blood, muscle, fat, bone, and perichondrium.

Recognition, selection and purification of stem cells carrying the cell surface markers described above can be effected by a number of different methods. For example, application of a binding agent to the marker concerned followed by a separation of those cells that exhibit binding, being either high level binding, or low level binding or no binding.

For example binding agents can include antibodies such as monoclonal antibodies or antibody based molecules.

Antibodies and other binding molecules can be used in various techniques to select and purify stem cells expressing the particular cell surface markers.

Techniques for selection and purification may include, but are not limited to, magnetic separation, using antibody-coated magnetic beads, affinity chromatography and "panning" with antibody attached to a solid matrix, fluorescence-activated cell sorting (FACS).

Stem cells of the present disclosure expressing particular markers may be selected or purified from a cell population via positive immunoselection. For example, mesenchymal precursor cells can be isolated and enriched from a cell population based on the cell surface expression of the STRO-1 antibody (see for example Gronthos and Simmons 1995).

Isolated stem cells according to the present disclosure can be expanded in vitro by culture. As will be appreciated by those skilled in the art, the stem cells can be cryopreserved, thawed and subsequently expanded in vitro by culture. In one example, the stem cells are seeded in growth medium and allowed to adhere to the culture vessel overnight at 37° C., 20% O2. The growth medium is subsequently replaced and the cells cultured for a further 68 to 72 hours at 37° C., 5% $O_2$.

In an example, isolated stem cells are seeded at 50,000 cells/cm$^2$ in serum supplemented growth medium and allowed to adhere to the culture vessel overnight at 37° C., 20% $O_2$. The growth medium is subsequently replaced with Chondrogenic Basal Medium (CBM; Lonza, Walkersville, Md.) supplemented with 0.5% bovine serum albumin (BSA) and the cells cultured for a further 68 to 72 hours at 37° C., 5% $O_2$.

Various other methods of primary stem cell culture are known in the art. For example, primary stem cell culture can be carried out using the methods described in Gronthos and Simmons 1995.

The cultured stem cells are phenotypically different to cells in vivo. They may express, for example, CD44.

In one embodiment the cultured stem cells are biologically different to cells in vivo, having a higher rate of regeneration.

The cultured stem cells may be cryopreserved prior to administration to a subject. For example, mesenchymal lineage precursor cells may be cryopreserved prior to administration to a subject.

Genetically-Unmodified Cells

As used herein, the term "genetically unmodified" refers to cells that have not been modified by transfection with a nucleic acid expressing or encoding Ang1. For the avoidance of doubt, in the context of the present disclosure a stem cell transfected with a nucleic acid encoding Ang1 would be considered genetically modified. In the context of the present disclosure the "genetically unmodified" cell naturally expresses Ang1 to some extent without transfection with a nucleic acid encoding Ang1.

Expression of Ang1 and/or VEGF

The stem cells of the present disclosure are genetically unmodified and express Ang1 in an amount of at least 0.1 $\mu g/10^6$ cells. However, in various embodiments it is envisaged that the stem cells of the present disclosure may express Ang1 in an amount of at least 0.2 $\mu g/10^6$ cells, 0.3 $\mu g/10^6$ cells, 0.4 $\mu g/10^6$ cells, 0.5 $\mu g/10^6$ cells, 0.6 $\mu g/10^6$ cells, 0.7 $\mu g/10^6$ cells, 0.8 $\mu g/10^6$ cells, 0.9 $\mu g/10^6$ cells, 1 $\mu g/10^6$ cells, 1.1 $\mu g/10^6$ cells, 1.2 $\mu g/10^6$ cells, 1.3 $\mu g/10^6$ cells, 1.4 $\mu g/10^6$ cells, 1.5 $\mu g/10^6$ cells.

In another aspect, the genetically unmodified stem cells of the present disclosure express VEGF in an amount less than about 0.05 $\mu g/10^6$ cells. However, in various embodiments it is envisaged that the stem cells of the present disclosure may express VEGF in an amount less than about 0.05 $\mu g/10^6$ cells, 0.04 $\mu g/10^6$ cells, 0.03 $\mu g/10^6$ cells, 0.02 $\mu g/10^6$ cells, 0.01 $\mu g/10^6$ cells, 0.009 $\mu g/10^6$ cells, 0.008 $\mu g/10^6$ cells, 0.007 $\mu g/10^6$ cells, 0.006 $\mu g/10^6$ cells, 0.005 $\mu g/10^6$ cells, 0.004 $\mu g/10^6$ cells, 0.003 $\mu g/10^6$ cells, 0.002 $\mu g/10^6$ cells, 0.001 $\mu g/10^6$ cells.

The amount of cellular Ang1 and/or VEGF that is expressed in a composition or culture of stem cells may be determined by methods known to those skilled in the art. Such methods include, but are not limited to, quantitative assays such as quantitative ELISA assays, for example. It is to be understood, however, that the scope of the present disclosure is not to be limited to any particular method for determining the amount or level of Ang1 or VEGF expressed in the stem cells of the present disclosure.

In one example the level of Ang1 or VEGF expressed by a composition or culture of stem cells is determined by an ELISA assay. In such an assay, a cell lysate from a culture of stem cells is added to a well of an ELISA plate. The well may be coated with a primary antibody, either a monoclonal or a polyclonal antibody(ies), against the Ang1 or VEGF. The well then is washed, and then contacted with a secondary antibody, either a monoclonal or a polyclonal antibody(ies), against the primary antibody. The secondary antibody is conjugated to an appropriate enzyme, such as horseradish peroxidase, for example. The well then may be incubated, and then is washed after the incubation period. The wells then are contacted with an appropriate substrate for the enzyme conjugated to the secondary antibody, such as one or more chromogens. Chromogens which may be employed include, but are not limited to, hydrogen peroxide and tetramethylbenzidine. After the substrate(s) is (are) added, the well is incubated for an appropriate period of time. Upon completion of the incubation, a "stop" solution is added to the well in order to stop the reaction of the enzyme with the substrate(s). The optical density (OD) of the sample is then measured. The optical density of the sample is correlated to the optical densities of samples containing known amounts of Ang1 or VEGF in order to determine the amount of Ang1 or VEGF expressed by the culture of stem cells being tested.

In another aspect, the genetically unmodified stem cells of the present disclosure express Ang1:VEGF at a ratio of at least about 2:1. However, in various embodiments it is envisaged that the stem cells of the present disclosure may express Ang1:VEGF at a ratio of at least about 10:1, 15:1, 20:1, 21:1, 22:1, 23:1, 24:1, 25:1, 26:1, 27:1, 28:1, 29:1, 30:1, 31:1, 32:1, 33:1, 34:1, 35:1, 50:1.

Methods for determining the Ang1:VEGF expression ratio will be apparent to one of skill in the art. In an example of a method of determining a ratio of Ang 1 and VEGF expression, Ang1 and VEGF expression levels are quantitated via quantitative ELISA as discussed above. In such an example, after quantifying the levels of Ang1 and VEGF, a ratio based on the quantitated levels of Ang1 and VEGF could be represented as: (level of Ang1/level of VEGF) =Ang1:VEGF ratio.

Cellular Compositions

In one example of the present disclosure stem cells are administered in the form of a composition. In one example, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g., saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. For example, such a media composition does not induce any adverse effects in a subject to whom it is administered.

Exemplary carriers and excipients do not adversely affect the viability of a cell and/or the ability of a cell to reduce, prevent or delay metabolic syndrome and/or obesity.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a tissue or a region surrounding or adjacent to a tissue, e.g., by injection.

Stem cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. J. Ped. Surg. 23:3-9 1988; Cima, et al. Biotechnol. Bioeng. 38:145 1991; Vacanti, et al. Plast. Reconstr. Surg. 88:753-9 1991; or synthetic polymers such as polyanhydrides, polyorthoesters, and polylactic acid.

In another example, the cells may be administered in a gel scaffold (such as Gelfoam from Upjohn Company).

The cellular compositions described herein may be administered alone or as admixtures with other cells. The cells of different types may be admixed with a composition of the disclosure immediately or shortly prior to administration, or they may be co-cultured together for a period of time prior to administration.

In one example, the composition comprises an effective amount or a therapeutically or prophylactically effective amount of cells. For example, the composition comprises about $1 \times 10^5$ stem cells with elevated Ang1 levels to about $1 \times 10^7$ stem cells with elevated Ang1 levels or about $1 \times 10^6$ stem cells to about $5 \times 10^6$ stem cells/kg. The exact amount of cells to be administered is dependent upon a variety of factors, including the age, weight, and sex of the subject, and the extent and severity of the disorder being treated.

In one example, a low dose of cells is administered to the subject. Exemplary dosages include between about $0.1 \times 10^4$ to about $0.5 \times 10^6$ cells per kg, for example, between about $0.1 \times 10^5$ to about $0.5 \times 10^6$ cells per kg, such as, between about $0.5 \times 10^5$ to about $0.5 \times 10^6$ cells per kg, for example, between about $0.1 \times 10^6$ to about $0.5 \times 10^6$ cells per kg, e.g., about $0.2 \times 10^6$ or $0.3 \times 10^6$ or $0.4 \times 10^6$ cells per kg.

In one example, a high dose of cells is administered to the subject. Exemplary dosages include at least about $1.5 \times 10^6$ cells/kg. For example, a high dose comprises between about $1.5 \times 10^6$ to about $6 \times 10^6$ cells/kg, such as between about $1.5 \times 10^6$ to about $5 \times 10^6$ cells/kg, for example, between about $1.5 \times 10^6$ to about $4 \times 10^6$ cells/kg, for example, between about $1.5 \times 10^6$ to about $3 \times 10^6$ cells/kg. For example, a high dose comprises about $1.5 \times 10^6$ or about $2 \times 10^6$ cells/kg.

Other exemplary doses include at least about $1 \times 10^6$ cells. For example, a dose can comprise between about $1.0 \times 10^6$ to about $1\times10^{10}$ cells, for example, between about $1.1\times10^6$ to about $1\times10^9$ cells, for example, between about $1.2\times10^6$ to about $1\times10^8$ cells, for example, between about $1.3\times10^6$ to about $1\times10^7$ cells, for example, between about $1.4\times10^6$ to about $9\times10^6$ cells, for example, between about $1.5\times10^6$ to about $8\times10^6$ cells, for example, between about $1.6\times10^6$ to about $7\times10^6$ cells, for example, between about $1.7\times10^6$ to about $6\times10^6$ cells, for example, between about $1.8\times10^6$ to about $5\times10^6$ cells, for example, between about $1.9\times10^6$ to about $4\times10^6$ cells, for example, between about $2\times10^6$ to about $3\times10^6$ cells.

In one example, the dose comprises between about $5\times10^5$ to $2\times10^7$ cells, for example, between about $6\times10^6$ cells to about $1.8\times10^7$ cells. The dose may be, for example, about $6\times10^6$ cells or about $1.8\times10^7$ cells.

The mesenchymal lineage precursor or stem cells comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% of the cell population of the composition.

In some examples, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors, e.g., implanted in or near the heart.

The stem cells of the present disclosure are administered to an animal in an amount effective to treat a disease or disorder in the animal. The animal may be a mammal, and the mammal may be a primate, including human and non-human primates. The stem cells may be administered systemically, such as, for example, by intravenous, intraarterial, or intraperitoneal administration. The exact dosage of stem cells to be administered is dependent upon a variety of factors, including, but not limited to, the age, weight, and sex of the patient, the disease(s) or disorder(s) being treated, and the extent and severity thereof.

The composition comprising stem cells of the present disclosure may be cryopreserved. Cryopreservation of stem cells can be carried out using slow-rate cooling methods or 'fast' freezing protocols known in the art. Preferably, the method of cryopreservation maintains similar phenotypes, cell surface markers and growth rates of cryopreserved cells in comparison with unfrozen cells.

The cryopreserved composition may comprise a cryopreservation solution. The pH of the cryopreservation solution is typically 6.5 to 8, preferably 7.4.

The cyropreservation solution may comprise a sterile, non-pyrogenic isotonic solution such as, for example, PlasmaLyte A®. 100 mL of PlasmaLyte A® contains 526 mg of sodium chloride, USP (NaCl); 502 mg of sodium gluconate ($C_6H_{11}NaO_7$); 368 mg of sodium acetate trihydrate, USP ($C_2H_3NaO_2.3H_2O$); 37 mg of potassium chloride, USP (KCl); and 30 mg of magnesium chloride, USP ($MgCl_2.6H_2O$). It contains no antimicrobial agents. The pH is adjusted with sodium hydroxide. The pH is 7.4 (6.5 to 8.0).

To facilitate freezing, a cryoprotectant such as, for example, dimethylsulfoxide (DMSO), is usually added to the cryopreservation solution. Ideally, the cryoprotectant should be nontoxic for cells and patients, nonantigenic, chemically inert, provide high survival rate after thawing and allow transplantation without washing. However, the most commonly used cryoprotector, DMSO, shows some cytotoxicity. Hydroxyethyl starch (HES) may be used as a substitute or in combination with DMSO to reduce cytotoxicity of the cryopreservation solution.

The cryopreservation solution may comprise one or more of DMSO, hydroxyethyl starch, human serum components and other protein bulking agents. In one example, the cryopreserved solution comprises about 5% human serum albumin (HSA) and about 10% DMSO. The cryopreservation solution may further comprise one or more of methylcellulose, polyvinyl pyrrolidone (PVP) and trehalose.

The cryopreserved composition may be thawed and administered directly to the subject. Alternatively, the cryopreserved composition may be thawed and the mesenchymal lineage precursor or stem cells resuspended in an alternate solution prior to administration.

Cell Culture Method

The compositions of the present disclosure can be produced via various cell culture methods.

Accordingly, the present disclosure also provides in vitro methods for inducing Ang1 expression in stem cells. Surprisingly, the present inventors have identified cell culture media conditions under which Ang1 expression is induced in stem cells. These conditions have also been found to reduce VEGF expression and induce an elevated ANG1:VEGF ratio.

For example, these conditions include culturing a population of stem cells in a cell culture media, wherein the cell culture media contains:
i) a short acting L-ascorbic acid derivative but does not contain a substantial amount of a long acting L-ascorbic acid derivative; and/or
ii) less than 10% v/v fetal calf serum.

In another example, these conditions include culturing a population of stem cells in a cell culture media, wherein the cell culture media contains:
i) a short acting L-ascorbic acid derivative but does not contain a substantial amount of a long acting L-ascorbic acid derivative;
ii) less than 10% v/v fetal calf serum; and/or
iii) a non-fetal serum.

Accordingly, in an embodiment, the present disclosure relates to an in vitro method for inducing Ang1 expression in stem cells, the method comprising: culturing a population of stem cells in a cell culture media, wherein the cell culture media contains a short acting L-ascorbic acid derivative but does not contain a substantial amount of a long acting L-ascorbic acid derivative; and/or is supplemented with less than 10% v/v fetal calf serum.

In another embodiment, the present disclosure relates to an in vitro method for inducing Ang1 expression in stem cells, the method comprising: culturing a population of stem cells in a cell culture media, wherein the cell culture media contains a short acting L-ascorbic acid derivative but does not contain a substantial amount of a long acting L-ascorbic acid derivative; and/or is supplemented with a non-fetal serum.

In another embodiment, the present disclosure relates to an in vitro method for inducing Ang1 expression in stem cells, the method comprising: culturing a population of stem cells in a cell culture media, wherein the cell culture media contains non-fetal serum in the form of human adult serum (for example, human AB serum) and human platelet cell lysate in amount sufficient to support growth of cells.

The term "media" or "medium" as used in reference to cell culture, includes the components of the environment surrounding the cells. It is envisaged that the media contributes to and/or provides the conditions sufficient to induce expression of Ang1 expression. Media may be solid, liquid, gaseous or a mixture of phases and materials. Media can include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells.

The culture media used in the method of the present disclosure can be prepared by using a culture media used for culturing of stem cells as a basal culture medium. The basal culture medium includes, for example, Eagles minimal essential (MEM) culture media, alpha modified MEM culture media, and mixed culture media thereof, and is not particularly restricted providing it can be used for culturing of stem cells.

Further, the culture medium of the present disclosure can contain any components such as fatty acids or lipids, vitamins, growth factors, cytokines, antioxidants, buffering agents, inorganic salts and the like.

The cell culture media used in the present disclosure contains all, essential amino acids and may also contain non-essential amino acids. In general, amino acids are classified into essential amino acids (Thr, Met, Val, Leu, Ile, Phe, Trp, Lys, His) and non-essential amino acids (Gly, Ala, Ser, Cys, Gln, Asn, Asp, Tyr, Arg, Pro).

Ascorbic Acid

Ascorbic acid is an essential supplement for the growth and differentiation of various kinds of cells in culture. It is now understood that particular ascorbic acid derivatives are "short acting" because they are not stable in solution, especially under the normal cell culture conditions of neutral pH and 37° C. These short acting derivatives rapidly oxidise into oxalic acid or threonic acid. In culture media (pH 7) at 37° C., oxidation decreases the level of these short acting ascorbic acid derivatives by approximately 80-90% in 24 hours. Accordingly, short acting ascorbic acid derivatives have been replaced with more stable "long acting" ascorbic acid derivatives in conventional cell culture of various cell types.

In the context of the present disclosure the term "short acting" encompasses ascorbic acid derivatives that are oxidised by approximately 80-90% following 24 hours of cell culture under culture conditions of neutral pH and 37° C. In one example, the short acting L-ascorbic acid derivative is a L-ascorbic acid salt. For example, in the context of the present disclosure, L-ascorbic acid sodium salt is a "short acting" ascorbic acid derivative.

In contrast, the term "long acting" encompasses ascorbic acid derivatives that are not oxidised by approximately 80-90% following 24 hours of cell culture under culture conditions of neutral pH and 37° C. In one example, in the context of the present disclosure, L-ascorbic acid-2-phosphate is a "long acting" ascorbic acid derivative. Other examples of long acting ascorbic acid derivatives include Tetrahexyldecyl Ascorbate Magnesium Ascorbyl Phosphate and 2-O-α-D-Glucopyranosyl-L-ascorbic acid.

The present inventors have surprisingly found that the replacement of a long acting ascorbic acid derivative with short acting derivative can induce Ang1 expression in stem cells. Therefore, in an embodiment of the present disclosure the cell culture media is supplemented with a short acting ascorbic acid derivative. For example, the cell culture media may contain at least about 0.005 g/L of a short acting ascorbic acid derivative. In another example, the cell culture media may contain at least about 0.01 g/L of a short acting ascorbic acid derivative. For example, the cell culture media may contain at least about 0.02 g/L of a short acting ascorbic acid derivative. In another example, the cell culture media may contain at least about 0.03 g/L of a short acting ascorbic acid derivative. For example, the cell culture media may contain at least about 0.04 g/L of a short acting ascorbic acid derivative. In another example, the cell culture media may contain at least about 0.05 g/L of a short acting ascorbic acid derivative. In another example, the cell culture media may contain at least about 0.06 g/L of a short acting ascorbic acid derivative. In one example of this embodiment, the cell culture media is supplemented with sodium salt of L-ascorbate.

In another example, the cell culture media contains a short acting ascorbic acid derivative but does not contain a substantial amount of a long acting ascorbic acid derivative. For example, the cell culture media may contain a short acting ascorbic acid derivative but not more than 0.04 g/L of a long acting ascorbic acid derivative. In another example, the cell culture media may contain a short acting ascorbic acid derivative but not more than 0.03 g/L of a long acting ascorbic acid derivative. In another example, the cell culture media may contain a short acting ascorbic acid derivative but not more than 0.02 g/L of a long acting ascorbic acid derivative. In another example, the cell culture media may contain a short acting ascorbic acid derivative but not more than 0.01 g/L of a long acting ascorbic acid derivative. In another example, the cell culture media may contain a short acting ascorbic acid derivative but not more than 0.005 g/L of a long acting ascorbic acid derivative. In another example, the cell culture media may contain a short acting ascorbic acid derivative but not a long acting ascorbic acid derivative.

In another example, the cell culture media contains L-ascorbate sodium salt but does not contain a substantial amount of L-ascorbic acid-2-phosphate.

Serum

The culture media used in the culture method of the present disclosure can be a serum-containing culture medium or a serum-free culture medium.

The culture medium of the present disclosure may contain or may not contain a serum replacement. The serum replacement can be, for example, albumin (for example, lipid-rich albumin), transferrin, fatty acid, insulin, collagen precursor, trace element, 2-mercaptoethanol or 3-thiol glycerol, or those appropriately containing serum equivalents. Such a serum replacement can be prepared, for example, by a method described in International Publication WO 93/30679, and commercially available products can also be used.

Conventionally, stem cells are maintained in cell culture using media supplemented with at least about 10-15% v/v serum, generally fetal calf serum (FCS). However, the present inventors have found that culturing a population of stem cells in a cell culture medium supplemented with less than 10% v/v FCS can also induce Ang1 expression. In an embodiment, a population of stem cells is cultured in a cell culture media supplemented with at least about 9% v/v, at least about 8% v/v, at least about 7% v/v, at least about 6% v/v, at least about 5% v/v, at least about 4% v/v, at least about 3% v/v, at least about 2% v/v, at least about 1% v/v FCS. It also is envisaged that the term fetal calf serum (FCS) and fetal bovine serum (FBS) can in the context of the present disclosure be used interchangeably.

In an embodiment, the cell culture media is supplemented with a non-fetal serum. It is envisaged that the culture media may be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v non-fetal serum.

For example, the culture media can be supplemented with mammalian non-fetal serum.

For example, the culture media can be supplemented with human non-fetal serum.

For example, the culture media can be supplemented with neo-natal serum. It is envisaged that the culture media may be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v neo-natal serum.

In an embodiment, the cell culture media is supplemented with mammalian neo-natal serum.

For example, the culture media can be supplemented with new born calf serum (NBCS). It is envisaged that the culture media may be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v NBCS.

In an embodiment, the cell culture medium is supplemented with human neo-natal serum.

For example, the cell culture medium can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9% v/v human neo-natal serum. For example, human neo-natal serum obtained from umbilical cord blood "cord blood".

In an embodiment, the culture media is supplemented with adult serum. It is envisaged that the culture media may be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v adult serum.

In an embodiment, the cell culture media is supplemented with mammalian adult serum.

For example, the cell culture medium can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v mammalian adult serum.

For example, the cell culture medium can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v adult bovine serum.

In an embodiment, the cell culture medium is supplemented with human adult serum.

For example, the cell culture medium can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9% v/v human adult serum.

For example, the cell culture medium can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9% v/v human AB serum.

In an example, the cell culture medium is supplemented with at least about 3% human AB serum.

In an embodiment the culture media is supplemented with a mixture of FCS and NBCS.

For example, the culture media can be supplemented with a mixture of FCS and NBCS so that the FCS:NBCS ratio is at least about 0.4:1, at least about 0.5:1, at least about 0.6:1, at least about 0.7:1, at least about 0.8:1, at least about 0.9:1, at least about 1:1, at least about 1.5:1, at least about 2:1.

For example, it is envisaged that the mixture of FCS and NBCS can comprise at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v of the cell culture media. However, in this example, the cell culture media is supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9% v/v, but less than 10% v/v FCS.

In an embodiment, the cell culture medium is FCS serum free.

In an embodiment, the cell culture medium is fetal serum free.

In an embodiment, the cell culture medium is supplemented with non-fetal serum.

In one embodiment the culture medium is fetal serum free and supplemented with non-fetal serum.

Stimulatory Factors

In another embodiment the cell culture media is supplemented with one or more stimulatory factors selected from the group consisting of 1α,25-dihydroxyvitamin D3 (1,25D), platelet derived growth factor (PDGF) such as PDGF-BB, tumor necrosis factor α (TNF-α), interleukin-1β (IL-1β), stromal derived factor 1α (SDF-1α) and EGF.

In another embodiment, cells may also be cultured in the presence of at least one cytokine in an amount sufficient to support growth of the cells.

In another embodiment, cells are cultured in the presence of platelet cell lysate in an amount sufficient to support growth of the cells. For example, cells can be cultured in human platelet cell lysate in an amount sufficient to support growth of the cells.

In an example, cells are cultured with human AB serum and human platelet cell lysate in an amount sufficient to support growth of the cells.

Assaying Therapeutic/Prophylactic Potential of Cells

Methods for determining the ability of the cells of the present disclosure to treat or prevent or delay the onset or progression of disorders will be apparent to one of skill in the art. For example, the present stem cells can be assessed for their ability to increase Ang1 levels.

In one example, genetically unmodified stem cells expressing Ang1 in an amount of at least 0.1 μg/$10^6$ cells are tested for their ability to increase Ang1 levels in vitro and/or in vivo in cardiac tissue. In these examples, Ang1 levels are assessed in cell culture medium or tissue after the administration of the presently described stem cells.

It will be apparent to the skilled artisan from the foregoing that the present disclosure also provides a method for identifying or isolating a cell for the treatment, prevention or delay of a disorder, the method comprising:

(i) administering a cell to a test subject suffering from a disorder associated and assessing a symptom of the disorder in the subject;

(ii) comparing the symptom of a disorder of the subject at (i) to the symptom of the disorder or activity of a control subject suffering from the disorder to which the cell has not been administered, wherein an improvement in the symptom in the test subject compared to the control subject indicates that the stem cell treats the disorder. The cell may be any cell described herein according to any example.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Example 1: Immunoselection of MPCs by Selection of STRO-3$^+$ Cells

Bone marrow (BM) is harvested from healthy normal adult volunteers (20-35 years old). Briefly, 40 ml of BM is aspirated from the posterior iliac crest into lithium-heparin anticoagulant-containing tubes.

BMMNC are prepared by density gradient separation using Lymphoprep™ (Nycomed Pharma, Oslo, Norway) as previously described (Zannettino et al. 1998). Following centrifugation at 400×g for 30 minutes at 4° C., the buffy layer is removed with a transfer pipette and washed three times in "HHF", composed of Hank's balanced salt solution (HBSS; Life Technologies, Gaithersburg, Md.), containing 5% fetal calf serum (FCS, CSL Limited, Victoria, Australia).

STRO-3$^+$ (or TNAP$^+$) cells were subsequently isolated by magnetic activated cell sorting as previously described (Gronthos et al. 2003; Gronthos and Simmons 1995). Briefly, approximately 1-3×$10^8$ BMMNC are incubated in blocking buffer, consisting of 10% (v/v) normal rabbit serum in HHF for 20 minutes on ice. The cells are incubated with 200 μl of a 10 μg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer ($Ca^{2+}$- and $Mn^{2+}$-free PBS supplemented with 1% BSA, 5 mM EDTA and 0.01% sodium azide) as above and resuspended in a final volume of 0.9 ml MACS buffer.

One hundred μl streptavidin microbeads (Miltenyi Biotec; Bergisch Gladbach, Germany) are added to the cell suspension and incubated on ice for 15 minutes. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International Publication No. WO 2006/108229). After addition of a further 1 ml MACS buffer, the column is removed from the magnet and the TNAP$^+$ cells are isolated by positive pressure. An aliquot of cells from each fraction can be stained with streptavidin-FITC and the purity assessed by flow cytometry.

The MPCs isolated in this manner are STRO-1$^{bright}$ MPCs.

Example 2: Starting Culture Media—Process A

The Alpha modification of Eagle's minimum essential media (MEM) with Earle's balanced salts, commonly referred to as Eagle's Alpha MEM, contains non-essential amino acids, sodium pyruvate, and additional vitamins. These modifications were first described for use in growing hybrid mouse and hamster cells (Stanners et al. 1971).

Eagle's Alpha MEM media suitable for culturing primary stem cells can be obtained from a variety of sources, including Life Technologies and Sigma.

A detailed method of establishing primary stem cell cultures, including the required growth factors used in the Exemplified processes is described in Gronthos and Simmons 1995.

In Process A, Eagle's Alpha MEM media supplemented with 10% fetal calf serum, L-ascorbate-2-phosphate (100 μM), dexamethasone (10-7 M) and/or inorganic phosphate (3 mM) was used for culturing stem cells.

Example 3: Modified Culture Media—Process B

In Process B, the Eagle's Alpha MEM culture media used in Process A was modified (modified Alpha MEM) by:
replacing the long acting ascorbic acid derivative L-ascorbic acid-2-phosphate with a short acting ascorbic acid derivative Sodium L-ascorbate (50 mg/L);
reducing FCS from 10% v/v to 5% v/v;
supplementing with non-fetal serum (5% v/v).

TABLE 1

Summary of the differences between Processes A and B

| Process A | Process B |
|---|---|
| Media (Change applicable to Thaw Feed, Passage) | |
| Alpha MEM<br>10% v/v FCS | Modified media<br>50 mg/L Sodium L-ascorbate replaces L-ascorbic acid-2-phosphate<br>5% v/v FCS<br>5% v/v non-fetal serum |
| | Cryopreservation Formulation<br>(50% Alpha-MEM/42.5% ProFreeze/7.5% DMSO) |
| Alpha MEM<br>10% v/v FCS | Modified Alpha MEM<br>50 mg/L Sodium L-ascorbate replaces L-ascorbic acid-2-phosphate<br>5% v/v FCS<br>5% v/v non-fetal serum |

Example 4: Cell Culture

Mesenchymal precursor cells (MPCs) were obtained from a single donor and stored following cryopreservation.

In general terms, cell culture involved the following steps:
Cryopreserved MPCs were thawed, seeded at 10,000 cells/cm$^2$, and grown in either starting culture medium (Process A; n=3) or modified culture medium (Process B; n=3) to 90% confluence at 20% O2, 37° C.

To generate conditioned medium, growth medium was replaced with EBM-2 basal medium (Lonza) supplemented with FCS at a volume of 200 μl medium/cm$^2$. Cells were cultured for an additional 3 days after which medium was collected and centrifuged to remove any cells and the resulting supernatant collected and stored at −80° C.

Growth factor concentrations were measured using the Luminex platform using commercially available kits (Millipore).

Figure 1:
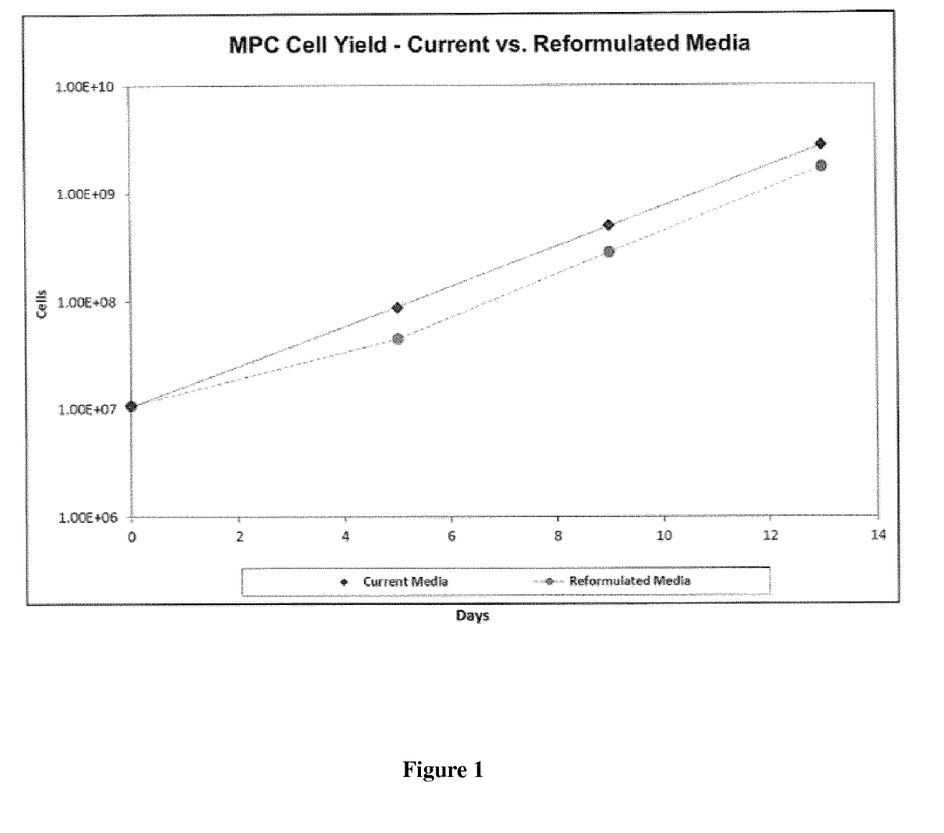
FIG. 1: MPC Growth with Process A and Process B. Y axis indicates cell numbers; X axis is time in days.
Figure 2:
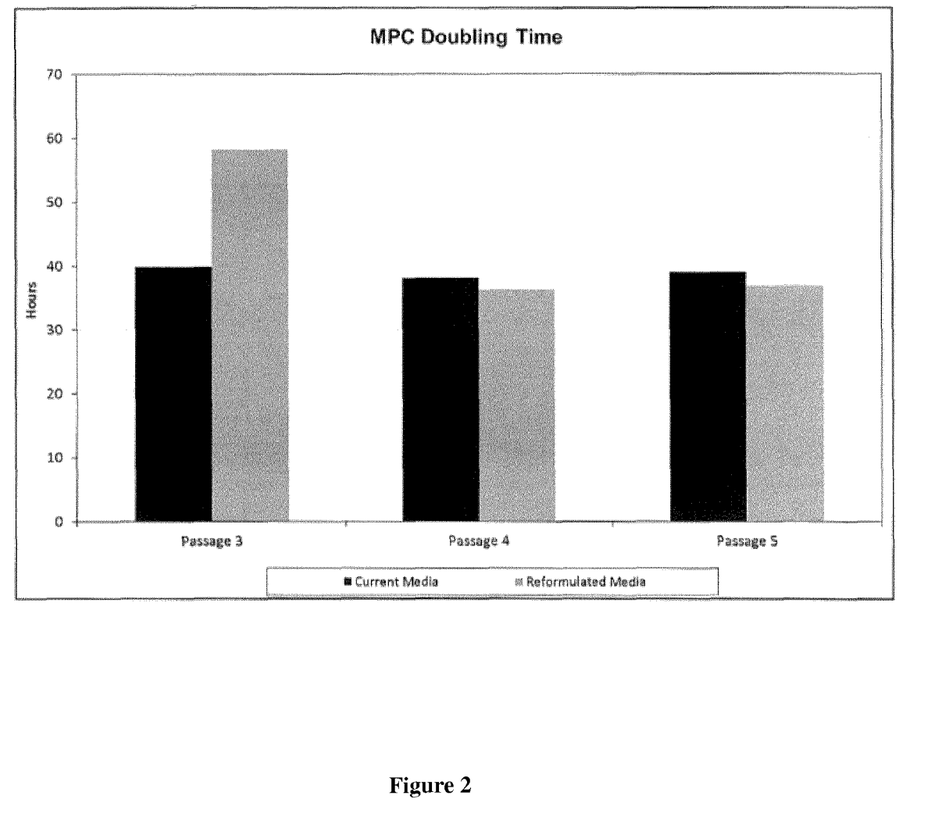
FIG. 2: MPC doubling times with Process A and Process B. Cells were passages from P3 to P5.
Figure 3:
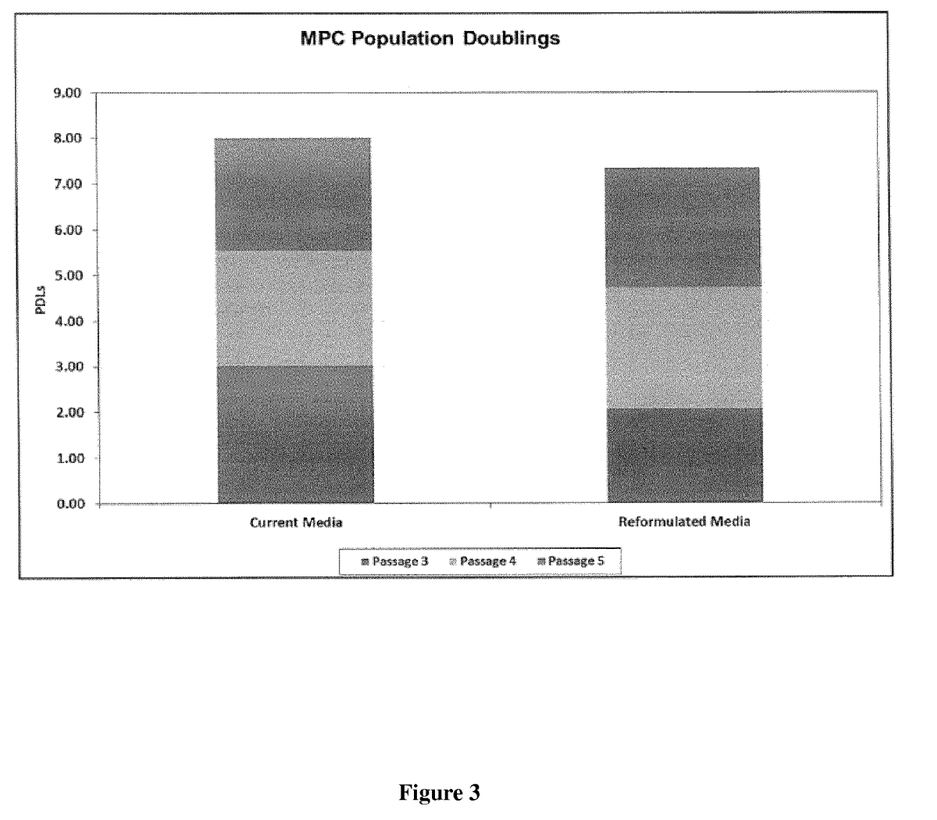
FIG. 3: Population Doubling Time (PDL) of MPCs with Process A and Process B. MPCs were grown from P3 to P5. MPCs grown with Process A underwent 8 PDL and MPCs grown with Process B underwent 7.33 PDL.

Following cell culture, MPC growth dynamics were assessed (see FIGS. 1-3). No significant changes in cell growth, MPC doubling times or population doubling times were observed following cell culture Processes A and B.

MPCs were also characterised in terms of their expression levels of cellular markers STRO-1, CC9 and STRO-4 as well as pro-angiogenic growth factors Ang1 and VEGF.

STRO-1, CC9 and STRO-4 levels were comparable in MPCs following cell culture Processes A and B.

However, culture Process B:
increased Ang1 levels;
reduced VEGF levels;
provided a ratio of Ang1:VEGF that was consistent with Ang1:VEGF ratios previously shown to be particularly effective in enhancing vascularization.

Measurement of the levels (ug/10$^6$ cells) of Ang1 and VEGF in the conditioned medium of MPCs cultured in Processes A or B are shown in Table 2.

TABLE 2

Characterisation of MPCs obtained from a single donor (three replicates) following Process A and B.

| Culture Process | Replicate | Ang 1 level ug/10$^6$ cells | Average | VEGF level ug/10$^6$ cells | Average | Ratio Ang1 level/VEGF level | Average |
|---|---|---|---|---|---|---|---|
| A | 1 | 0.048 | 0.045 | 0.134 | 0.14 | 0.358:1 | 0.328:1 |
| A | 2 | 0.059 | | 0.172 | | 0.343:1 | |
| A | 3 | 0.029 | | 0.102 | | 0.284:1 | |
| B | 1 | 0.733 | 0.72 | 0.027 | 0.025 | 27.1:1 | 29.6:1 |
| B | 2 | 0.717 | | 0.020 | | 35.9:1 | |
| B | 3 | 0.723 | | 0.028 | | 25.8:1 | |

Example 5: Modified Culture Conditions—Processes C and D

To control for the replacement of the long acting ascorbic acid derivative L-ascorbic acid-2-phosphate with a short acting ascorbic acid derivative Sodium L-ascorbate, MPC's from 3 different donors were serially propagated in alpha-MEM+10% FCS+50 mg/L Sodium L-ascorbate (Process C) or alpha-MEM+3% human AB serum+50 mg/L Sodium L-ascorbate (Process D)+growth factors such as PDGF and EGF.

Ang1 and VEGF levels were assessed following cell culture in Processes C and D. The levels (ug/ml) of Ang1 and VEGF in the conditioned medium of MPCs cultured in Processes C or D are shown in Table 3.

Compared with Process C, culture Process D:
increased Ang1 levels;
reduced VEGF levels;
increased the ratio of Ang1:VEGF.

Compared with Process A, Processes C and D resulted in progressive increases in the expression levels of Ang1. This suggests that the presence of a short acting ascorbic acid derivative and non-fetal serum each independently result in increased Ang1 expression and together exhibit a synergistic effect in increasing Ang1 expression.

TABLE 3

Characterisation of MPCs from 3 different donors following Process C and D.

| Culture Process | Donor Sample | Ang 1 level ug/$10^6$ cells | Average | VEGF level ug/$10^6$ cells | Average | Ratio Ang1 level/VEGF level | Average |
|---|---|---|---|---|---|---|---|
| C | 1 | 0.143 | 0.136 | 0.430 | 0.328 | 0.333:1 | 0.409:1 |
| C | 2 | 0.164 |  | 0.266 |  | 0.523:1 |  |
| C | 3 | 0.102 |  | 0.287 |  | 0.370:1 |  |
| D | 1 | 0.266 | 0.191 | 0.164 | 0.109 | 1.73:1 | 2.11:1 |
| D | 2 | 0.164 |  | 0.061 |  | 3.20:1 |  |
| D | 3 | 0.143 |  | 0.102 |  | 1.40:1 |  |

It will be appreciated by persons skilled in the art that numerous variations and/or modifications may be made to the disclosure as shown in the specific embodiments without departing from the spirit or scope of the disclosure as broadly described. The present embodiments are, therefore, to be considered in all respects as illustrative and not restrictive.

The present application claims priority from AU 2014901247 filed 7 Apr. 2014, the disclosures of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

REFERENCES

1. Bongso et al. 1889, Improved quality of human embryos when co-cultured with human ampullary cells. Human Reprod., 4(6), 706-13.
2. Chae et al. 2000, Coadministration of angiopoietin-1 and vascular endothelial growth factor enhances collateral vascularization. Arterioscler. Thromb. Vasc. Biol. 20, 2573-2578.
3. Eisenberg & Bader, 1996, Establishment of the mesodermal cell line QCE-6. A model system for cardiac cell differentiation. Circ Res., 78(2), 205-16.
4. Gnecchi et al. 2008, Paracrine mechanisms in adult stem cell signalling and therapy. Circ Res., 103(11), 1204-1219.
5. Huang et al. 2011, Transplantation of Sendai Viral Angiopoietin-1-Modified Mesenchymal Stem Cells for Ischemic Heart Disease. Targets in Gene Therapy, Prof. Yongping You (Ed.), ISBN: 978-953-307-540-2, InTech, DOI: 10.5772/19590. Available from: http://www.intechopen.com/books/targets-in-gene-therapy/transplantation-of-sendai-viral-angiopoietin-1-modified-mesenchymal-stem-cells-for-ischemic-heart-di.
6. Gronthos and Simmons 1995, The growth factor requirements of STRO-1-positive human bone marrow derived stromal precursors under serum-deprived conditions in vitro. Blood, 85, 929-940.
7. Gronthos et al. (2003) Molecular and cellular characterisation of highly purified stromal stem cells derived from human bone marrow. Journal of Cell Science 116: 1827-1835
8. Kanatsu-Shinohara et al. 2003, Long-term proliferation in culture and germline transmission of mouse male germline stem cells, Biol. Reprod., 69(2), 612-616.

9. Kim et al. 2001a, Angiopoietin-1 reduces VEGF-stimulated leukocyte adhesion to endothelial cells by reducing ICAM-1, VCAM-1, and E-selectin expression. Circ Res., 89(6), 477-479.
10. Kim et al. 2001b, Angiopoietin-1 negatively regulates expression and activity of tissue factor in endothelial cells. FASEB J., 16(1), 126-128.
11. Lijie et al. 2007, Mesenchymal stem cells modified with angiopoietin-1 improve remodelling in a rat model of acute myocardial infarction. Biochem Biophys Res Commun., 357(3), 779-84.
12. Matsui et al. 1992, Derivation of pluripotential embryonic stem cells from murine primordial germ cells in culture. Cell, 70(5): 841-7.
13. Mummery et al. 2002, Cardiomyocyte differentiation of mouse and human embryonic stem cells. J Anat., 200(3), 233-242.
14. Passier R et al. 2005, Increased cardiomyocyte differentiation from human embryonic stem cells in serum-free cultures. Stem Cells, 23(6), pg 772-80.
15. Resnick et al. 1992, Long-term proliferation of mouse primordial germ cells in culture. Nature, 359(6395), 550-551.
16. Reubinoff et al. 2000, Embryonic stem cell lines from human blastocysts: somatic differentiation in vitro. Nat Biotechnol., 18(4), 399-404.
17. Shamblott et al. 1998, Derivation of pluripotent stem cells from cultured human primordial germ cells, Proc. Natl. Acad. Sci. USA, 95(23), 13726-31.
18. Shinohara et al. 2004, Generation of pluripotent stem cells from neonatal mouse testis, Cell, 119(7), 1001-1012.
19. Stanners et al., 1971, Two Types of Ribosome in Mouse-Hamster Hybrid Cells. Nat New Biol., 230, 52-54.
20. Takebayashi et al. 2008, Experimental Medicine, 26(5) (Suppl.), 41-46, YODOSHA (Tokyo, Japan).
21. Thomson et al. 1995, Isolation of a primate embryonic stem cell line, Proc. Natl. Acad. Sci USA, 92(17), 7844-8.
22. Thomson et al. 1996, Pluripotent cell lines derived from common marmoset (Callithrix jacchus) blastocysts. Biol. Reprod., 55(254), 254-9.
23. Thomson et al. 1998, Embryonic stem cell lines derived from human blastocysts. Science, 282, 1145-7.
24. Vacanti, et al. 1991, Synthetic polymers seeded with chondrocytes provide a template for new cartilage formation. Plast. Reconstr. Surg. 88, 753-9.
25. Yoshiaki et al. 2012, Human periodontal ligament fibroblasts are the optimal cell source for induced pluripotent stem cells. Histochemistry & Cell Biology, 137(6), 719-732.
26. Zannettino, A. C. et al. 1998, The Sialomucin CD164 (MGC-24v) Is an Adhesive Glycoprotein Expressed by Human Hematopoietic Progenitors and Bone Marrow Stromal Cells That Serves as a Potent Negative Regulator of Hematopoiesis. Blood 92: 2613-2628.

The invention claimed is:

1. A composition comprising a population of culture expanded, genetically unmodified mesenchymal precursor cells (MPCs), wherein the culture expanded cells express angiopoietin-1 (Ang1) and vascular endothelial growth factor (VEGF) at an Ang1:VEGF ratio between 2:1 and 30:1.

2. The composition of claim 1, wherein said MPCs express Ang1:VEGF at a ratio between 5:1 and 20:1.

3. The composition of claim 1, wherein said MPCs express Ang1 in an amount between 0.1 µg/$10^6$ cells and 1.0 µg/$10^6$ cells.

4. The composition of claim 1, wherein said MPCs express Vascular Endothelial Growth Factor (VEGF) in an amount less than 0.05 µg/$10^6$ cells.

5. The composition of claim 1, wherein said MPCs express VEGF in an amount less than 0.03 µg/$10^6$ cells.

6. A composition according to claim 1, wherein the MPCs are produced by culture expanding a population of MPCs in vitro, wherein the culture expanding comprises: culturing a population of MPCs in a cell culture medium, which contains an L-ascorbic acid sodium salt; and/or
is supplemented with less than 10% v/v fetal calf serum (FCS); and/or
is supplemented with a non-fetal serum.

7. A composition according to claim 1, wherein the cells are culture expanded in a culture medium which:
(a) comprises an L-ascorbic acid sodium salt; and/or
(b) is supplemented with less than 10% v/v fetal calf serum (FCS); and/or
(c) is supplemented with a non-fetal serum.

* * * * *